United States Patent [19]

Horton et al.

[11] Patent Number: 5,234,420

[45] Date of Patent: Aug. 10, 1993

[54] COLLECTION CHAMBER SUPPORT DEVICE

[76] Inventors: Ronald E. Horton; M. Irene Horton, both of Rte. 5 Box 207, Floresville, Tex. 78114

[21] Appl. No.: 878,276

[22] Filed: May 4, 1992

[51] Int. Cl.⁵ .......................... A61M 1/00; A61F 5/44
[52] U.S. Cl. ................................. 604/345; 224/226; 604/327
[58] Field of Search .............. 604/345, 327, 332, 353, 604/317, 331, 349, 392, 398, 400; 224/224, 226

[56] References Cited

U.S. PATENT DOCUMENTS

| | | | |
|---|---|---|---|
| 1,015,801 | 1/1912 | Jennings | 224/226 |
| 1,705,194 | 3/1929 | Marinsky | 604/400 |
| 3,212,690 | 10/1965 | Green | 224/224 |
| 4,122,851 | 10/1978 | Grossner | 604/353 |
| 4,421,509 | 12/1983 | Schneider et al. | 604/327 |
| 4,511,358 | 4/1985 | Johnson et al. | 604/345 |
| 4,846,816 | 7/1989 | Manfredi | 604/353 |
| 4,955,879 | 9/1990 | Mervine | 604/327 |
| 5,026,362 | 6/1991 | Willett | 604/345 |
| 5,087,251 | 2/1992 | Heyman et al. | 604/327 |

*Primary Examiner*—Paul J. Hirsch
*Attorney, Agent, or Firm*—Viviana Amzel

[57] ABSTRACT

Apparatus for supporting a drainage catheter collection chamber to a body portion of a patient in a comfortable, non-irritating manner including a sheet of soft fiber material having a loop portion formed on at least one edge thereof, at least two tabs extending from corner portions of the loop portion, male snap fastener portions affixed to the loop portion, and female snap fastener portions affixed to the tabs in such a manner that when the tabs are folded over the loop portion the male and female snap fastener portions are in alignment to be engaged with each other.

4 Claims, 3 Drawing Sheets

COLLECTION CHAMBER SUPPORT DEVICE

BACKGROUND OF THE INVENTION

1. Field of the Invention

The present invention relates generally to a support device for a collection chamber, and more particularly to a support device which is attached to a drainage catheter collection chamber which does not alter the structure of existing collection chambers.

2. Description of the Background

Drainage catheter collector chambers are conventionally made in the form of plastic bags having openings in the four corners thereof for receiving rubber straps which are utilized to attach the collection chamber to the body portion of a patient. The plastic collection chamber and rubber strapping are in direct contact with the skin of the patient, which may cause discomfort and irritation. In order to overcome such discomfort and irritation, it has become standard practice in hospitals to attach the collection chamber to the hospital gown or clothing of the patient utilizing safety pins. A further practice has been to attach the collection chamber to the bedpost or to a metal support pole which can be moved with the patient. It is highly undesirable to create a situation where the catheter will have a tendency to pull away from the patient at the point where the catheter is stitched to the patient's skin. However, by attaching the collection chamber to the patient's hospital gown or to an external support, pulling on the catheter frequently occurs, creating discomfort to the patient and possible dislodging of the catheter.

SUMMARY OF THE INVENTION

It is therefore an object of the present invention to provide a support device for a drainage catheter collection chamber which may be attached to a patient's body in a comfortable and safe manner.

A further object of this invention is to provide a support device for a drainage catheter collection chamber which can be attached to a patient's body without creating discomfort, irritation, and which does not have a tendency to pull the catheter away from the patient.

It is a further object of the present invention to provide a support device for a drainage catheter collection chamber which is comfortable, non-irritating to the skin, completely mobile with the patient, and yet does not necessitate the altering of the basic structure of an existing collection chamber.

BRIEF DESCRIPTION OF THE DRAWINGS

The invention will be further described in conjunction with the accompanying drawings, in which.

DETAILED DESCRIPTION OF THE PREFERRED EMBODIMENTS

Figure 1:
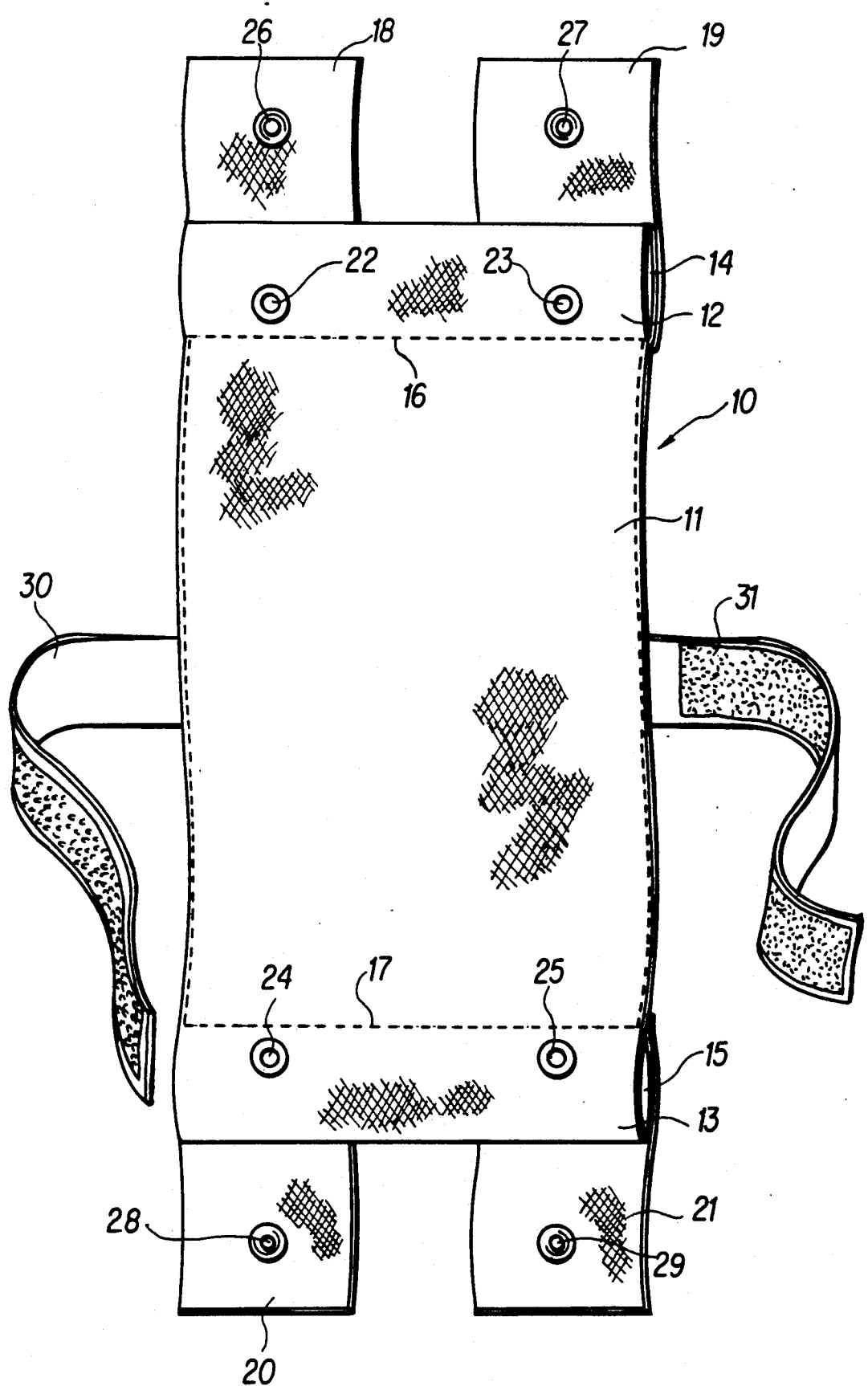
FIG. 1 is a front plan view of the support device of the present invention.

With reference to the figures, wherein like reference characters indicate like elements throughout the several views and, in particular, with reference to FIG. 1, the collection chamber support device 10 includes a body portion 11 constructed of a sheet of soft fiber material such as cotton cloth. Loop portions 12 and 13 are formed at the respective ends of body portion 11 to provide elongated open passages 14 and 15 for receiving support belts 37 and 39, as more clearly seen in FIGS. 2, 3 and 4. Loops 12 and 13 may be integrally formed with body portion 11 or may be stitched thereto, as shown at 16 and 17. Tabs 18, 19, 20 and 21 extend longitudinally from loop portions 12 and 13 at the four corners of the support device and have a female snap portion 26, 27, 28 and 29, respectively, affixed thereto for engagement with male snap portions 22, 23, 24 and 25 affixed to loop portions 12 and 13. Holding straps 30 and 31 are fixed to body portion 11 by stitching or the like and are constructed of VELCRO or other self-sticking material.

Figure 2:
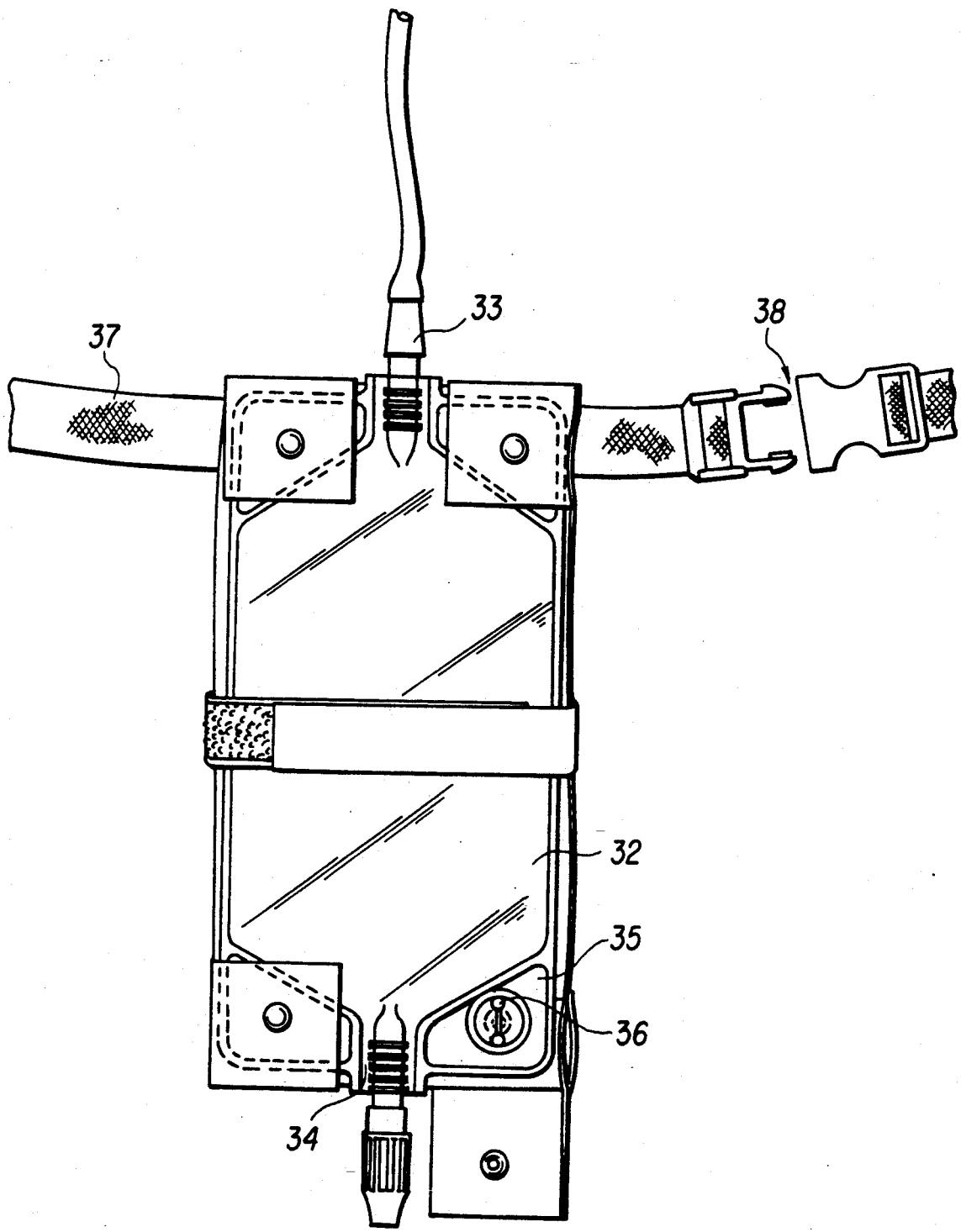
FIG. 2 is a front plan view of the support device of the present invention with a collection chamber and a support belt attached thereto.
Figure 3:
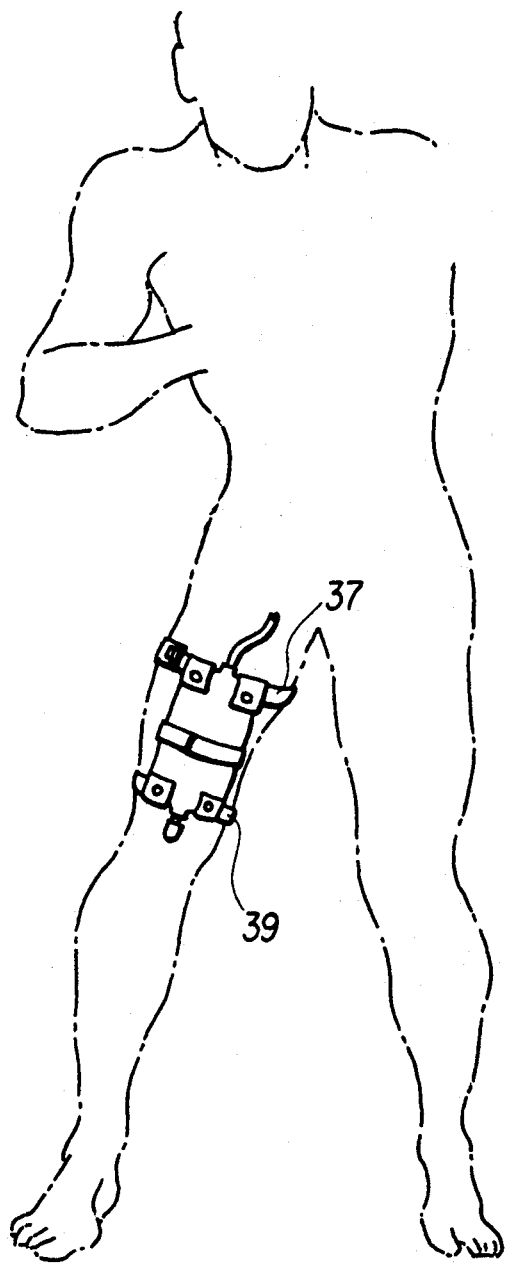
FIG. 3 is a cut-away view of a patient's body having the support device and collection chamber of the present invention attached to the leg portion thereof.
Figure 4:
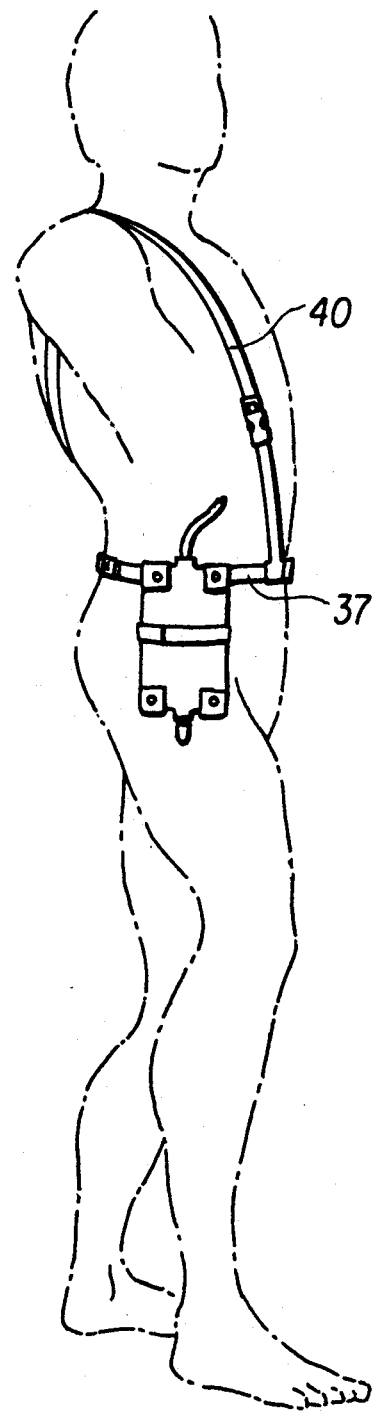
FIG. 4 is a cut-away view of a patient wearing the support device and collection chamber with a support belt arrangement such that the collection chamber is carried by the torso portion of the body.

Referring not to FIGS. 2, 3 and 4, a collection chamber 32 in the form of a plastic bag, including an input portion 33 and an output portion 34, is attached to the collection chamber support device 10. The collection chamber 32 includes a reinforced portion 35 at each of the four corners thereof with a key slot opening 36 located at the reinforced portion. The male snap portions 22, 23, 24 and 25 extend through the openings 36 such that when the tabs 18, 19, 20 and 21 are folded over the reinforced portions 35, female snap portions 26, 27, 28 and 29 come into engagement with the male snap portions thereof to secure the collection chamber 32 to the support device 10. Holding straps 30 and 31 are wrapped around the collection chamber 32 to assure that the body portion 11 of the support device covers one side of the collection chamber such that when the support device is brought into contact with the human body, it separates the body from the collection chamber.

As shown in FIGS. 2, 3 and 4, an upper support belt 37 extends through elongated open passage 14 and includes an adjustable bayonet and clasp type connector 38 such that the support device 10 and collection chamber 32 may be adjustably attached to a human body at a leg portion, as shown in FIG. 3, or to a waist portion, as shown in FIG. 4. When the support device is attached to a limb portion, as shown at FIG. 3, a lower support belt 37 may also be provided. When the collection chamber is to be attached around the waist portion of a human being, as shown in FIG. 4, an adjustable shoulder belt 40 may be secured to the upper support belt 37, as shown in FIG. 4.

Although the present invention has been fully described in connection with the preferred embodiment thereof with reference to the accompanying drawings, it is to be noted that various changes and modifications are apparent to those skilled in the art. Such changes and modifications are to be understood as included within the scope of the present invention as defined by the appended claims, unless they depart therefrom.

What is claimed as novel in U.S. Letters Patent is:

1. Apparatus for supporting a drainage catheter collection chamber to a body portion of a patient in a comfortable non-irritating manner comprising:

a sheet of soft fiber material;

a first loop portion formed on at least one edge of said sheet;

at least two tabs extending from corner portions of said first loop portion;

male snap fastener portions being affixed to said loop portion; and female snap fastener portions being affixed to said tabs in such a manner that when said tabs are folded over said loop portion, said male and female snap fastener portions are in alignment to be engaged with each other.

2. Apparatus according to claim 1 wherein:

a second loop portion is formed on an opposite edge of said sheet from said first loop portion;

at least two tabs extending from corner portions of said second loop portion;

male snap fastener portions being affixed to said second loop portion; and female snap fastener portions being affixed to all of said tabs.

3. Apparatus according to claim 2 wherein: self sticking holding straps are affixed to said sheet for engagement around said collection chamber.

4. A drainage catheter collection chamber and support device therefor comprising:

an opening in each of the corners of said collection chamber;

a sheet of soft fiber material substantially covering one face of said collection chamber;

loop portions formed on opposite edges of said sheet;

tabs extending from corner portions of said loop portions;

male snap fastener portions being affixed to said loop portions and extending through said openings in each of said corners of said collection chamber; and female snap fastener portions being affixed to each of said tabs in such a manner that when said tabs are folded over said loop portions, said male and female snap fastener portions are engaged with each other to secure said support device to said collection chamber.

* * * * *